United States Patent [19]

Delattre et al.

[11] 4,163,860

[45] Aug. 7, 1979

[54] PROCESS FOR OBTAINING DIMETHYL TEREPHTHALATE FROM POLYESTER SCRAP

[75] Inventors: Jacques Delattre, Ste-Foy-les-Lyon; Roland Raynaud, Villeurbanne; Claude Thomas, Brignais, all of France

[73] Assignee: Rhone-Poulenc-Textile, Paris, France

[21] Appl. No.: 748,540

[22] Filed: Dec. 8, 1976

[30] Foreign Application Priority Data

Dec. 16, 1975 [FR] France .................................. 75 38775
Oct. 26, 1976 [FR] France .................................. 76 32484

[51] Int. Cl.² .............................................. C07C 69/82
[52] U.S. Cl. ........................................ 560/96; 560/78; 560/92
[58] Field of Search ............... 260/475 R, 491, 475 D; 560/96

[56] References Cited

U.S. PATENT DOCUMENTS

2,476,052  7/1949  Lippincott ........................... 260/491
3,784,578  1/1974  Swodenk et al. .................... 260/491

FOREIGN PATENT DOCUMENTS

1081681  12/1954  France .................................. 260/475 R

*Primary Examiner*—Jane S. Myers
*Attorney, Agent, or Firm*—Stevens, Davis, Miller & Mosher

[57] ABSTRACT

A process is disclosed for converting a bis-(diol) terephthalate to dimethyl terephthalate, by interchange in a methanol medium in the presence of magnesium methylate as catalyst. In this way dimethyl terephthalate may be regenerated from scrap of polyterephthalate or copolyterephthalate filaments or films, for the purpose of manufacturing fresh polyterephthalates or copolyterephthalates which can then be used for the manufacture of, for example, filaments or films.

14 Claims, No Drawings

PROCESS FOR OBTAINING DIMETHYL TEREPHTHALATE FROM POLYESTER SCRAP

This invention relates to a process for regenerating polyterephthalate or copolyterephthalate scrap, and in particular to the conversion of diglycol terephthalate ("DGT") or the terephthalate of other bis-diols to dimethyl terephthalate ("DMT") by methanol interchange.

In the manufacture of poly(ethylene terephthalate) the starting material is generally DMT which is reacted with ethylene glycol so as to form DGT (i.e., the diester of glycol and terephthalic acid) by glycol interchange, this compound then being polycondensed to give poly(ethylene terephthalate).

Similarly, for the manufacture of other polyterephthalates or copolyterephthalates the starting material is generally DMT, which is reacted with one or more diols and optionally with the dimethyl ester or another copolymerizable acid.

If it is desired to recover poly(ethylene terephthalate) scrap, for example in the form of filaments, films or other articles, a depolymerization by glycolysis is first carried out so as to obtain DGT, which is not recycled directly because it is too difficult to purify, but is converted to DMT by methanol interchange.

Similarly, in order to depolymerize a polyterephthalate of another diol, the depolymerization is carried out by diolysis, using the same diol as that from which the polymer was produced, thus giving a bis-(diol) terephthalate.

The use of various metals, and in particular magnesium, in various forms as glycol interchange catalysts, for the conversion of DMT to DGT in the course of the manufacture of polyesters is well known. Thus, this interchange can be effected in the presence of magnesium oxide in accordance with French Pat. No. 1,240,184, or in the presence of magnesium oxide, carbonate or glycolate in accordance with French Pat. No. 1,227,089, or, finally, in the presence of methylates of alkali metals or alkaline earth metals in accordance with French Pat. No. 919,729.

Furthermore, it is known from U.S.S.R. Pat. No. 146,736 to convert poly(ethylene terephthalate) fiber scrap to DGT by glycolysis in the presence of carbonates or acetates of magnesium, sodium or other metals as catalysts. However, while such compounds have a significant catalytic activity as far as the depolymerization of the polyesters in a glycol medium at about 180° C. is concerned, they exhibit no catalytic activity whatsoever as far as the methanol interchange of DGT to DMT is concerned, which is generally carried out in the presence of sodium hydroxide.

In addition, French Pat. No. 1,081,681 relates to the depolymerization, followed by the methanolysis of diglycol terephthalate in the presence principally of sodium hydroxide, a sodium alcoholate or possibly potassium hydroxide, a potassium alcoholate or alkaline earth metal alcoholates.

Finally, French Pat. No. 1,164,112 describes the decomposition of poly(ethylene terephthalate) by heating it under relatively high pressure (e.g., a pressure of 10 to 19 atmospheres) in the presence of dimethyl terephthalate, methanol and a catalyst chosen from amongst zinc, oxides and acetates of zinc and of lead, magnesium, magnesium oxide and iron.

This invention relates to a process for the conversion of a bis-(diol) terephthalate, obtained by diolysis of a polyterephthalate or copolyterephthalate, to dimethyl terephthalate by interchange in a substantially anhydrous methanol medium in the presence of magnesium methylate as the catalyst. Preferably methanol does not contain more than 3,000 ppm of water.

The methanol interchange is carried out on the bis-(diol) terephthalate in solution in the diol obtained by diolysis of the polyester scrap which may be ground beforehand. If desired, the diolysate obtained in this operation may be concentrated by distilling a little of the diol so as to give, for example, a solution of bis-(diol) terephthalate, referred to as BDT in the remainder of the text, having a concentration of 70% by weight in the diol.

The methanol interchange process according to the present invention is carried out with a very large excess of methanol, which at one and the same time plays the chemical role of converting the BDT to DMT, and the role of bringing into suspension the DMT thus formed. It is generally preferred to use an amount by weight of methanol at least equal to the amount of BDT present in the diol solution to be treated, but this amount may amount to, or even exceed, two or even three times the weight of BDT, so as to give a suspension which is easier to handle and transport.

The magnesium methylate used in accordance with the present invention may be introduced into the reaction medium in solid form or in solution, preferably in methanol solution. It may be prepared by reacting magnesium metal with methanol at ordinary temperature or at a higher temperature, if appropriate in the presence of traces of catalyst, for example mercuric chloride and iodine. The reaction may be accelerated by raising the temperature to the boiling point of the methanol, but a limit is imposed on the temperature chosen by the rate at which hydrogen is formed by the reaction.

In view of the various forms of crystallization or solvation of magnesium methylate, the amounts of catalyst will, in the test which follows, be expressed for greater convenience as weight of magnesium metal, even though only the methylate form is suitable for carrying out the invention.

The amount of catalyst which may be used in accordance with the present invention is at least 250 ppm of magnesium relative to the weight of BDT to be converted, and preferably at least 1,000 ppm, and may reach or even exceed 3,000 ppm and at times 7,000 ppm. It must be noted, however, that the amount of catalyst to be used depends equally on the other reaction conditions and in particular to a large degree on the water content of the methanol, which must remain low.

The reaction temperature of the methanol interchange according to the present invention may vary within wide limits, for example, between room temperature and the boiling point of the reaction mixture (about 70° C. at atmospheric pressure). However, the conversion of the BDT to DMT takes place with intermediate formation of the mixed methyl/diol terephthalate (MDT). The first stage of the conversion of BDT to MDT takes place more rapidly at a fairly high temperature, for example of the order of 70° C., while the second stage of the conversion of MDT to DMT takes place more rapidly at a temperature below 50° C. and even below 30° C., for example at 25° C.

It will thus be generally desirable to cause the reaction to start at a relatively high temperature, for example at about 70° C., and to maintain this temperature for several hours, and then to lower the temperature to 25°–30° C., for example, again, in 1 to 2 hours, and finally to maintain this lower temperature for several hours longer, until the conversion of BDT to DMT is almost complete.

Though on an industrial scale it is of advantage to work at atmospheric pressure, one may also work under (elevated) pressure in the first stage of the reaction and obtain similar results.

The process according to this invention may be carried out continuously or discontinuously.

At the end of the reaction, the DMT is separated from its suspension by per se known means such as filtration, centrifuging, decanting and the like, and may then, if necessary or desired, be purified, also by per se known means, such as washing, recrystallization from methanol, distillation, and the like.

The process according to this invention gives a DMT which, after purification, is of a quality which is equal to or better than the quality of a DMT obtained by other industrial processes.

The methanol filtrates contain the diol from the reaction, terephthalate residues (dissolved DMT, MDT and other reaction intermediates), and various impurities already present in the scrap.

In the case of the methanolysis of DGT, the methanol may be recovered by distillation of these filtrates under reduced pressure thereby obtaining a glycol suspension from which the DMT is isolated by filtration.

This recovery of methanol may also be effected by distilling these filtrates at ordinary atmospheric pressure, during which the temperature reached causes the conversion of the DMT to glycol esters dissolved in the ethylene glycol.

This ethylene glycol containing esters may be recycled, before purification, for the glycolysis of fresh scrap. It contains magnesium residues in sufficient amount to catalyze this glycolysis and glycol esters which are additional to the DGT formed in the new glycolysis, and may be converted to DMT in the course of a fresh methanol interchange operation. They thus lead to a desirable increase in the overall yield.

The ethylene glycol may also be purified by distillation. The ethylene glycol thus obtained may be used advantageously for the manufacture of a poly(ethylene terephthalate) of very good quality.

In the case of the methanolysis of other bis(diol) terephthalates, the recovery techniques will be adapted to the particular products in question.

The process according to the present invention may be applied without difficulty to scrap of any terephthalate polyesters and copolyesters such as, for example, poly(propylene terephthalate), poly(butylene terephthalate), poly(hexylene terephthalate), poly(cyclohexyldimethylene terephthalate), or terephthalate-isophthalate copolyesters, again with ethylene, propylene, butylene, hexylene, cyclohexyldimethylene and the like as the diol radicals.

Compared to the heretofore known processes of methanol interchange with alkaline catalysis (using sodium hydroxide, sodium methylate and the like), the process according to the present invention exhibits a higher yield which in general is even quantitative. In effect, sodium hydroxide irreversibly converts, for example, DGT, GMT (the mixed glycol/methyl terephthalate), and DMT to monosodium and disodium terephthalates, while no equivalent reaction whatsoever takes place with magnesium methylate under the conditions of the present process.

Finally, the process according to this invention is cleaner from the ecological point of view because it gives a smaller amount of by-products to be destroyed. Furthermore, while the incineration of materials containing organic magnesium salts does not present serious difficulties, the incineration of sodium salts is a delicate matter because these salts can destroy refractories and necessitate the use of special incineration techniques or a resort to biological destruction.

The examples which follow, in which the parts and percentages are by weight, are given by way of indication and in order still better to illustrate the invention without in any way limiting it.

EXAMPLE 1

The glycolysis of polyester scrap containing 97% of poly(ethylene terephthalate) is carried out using 1 part of ethylene glycol per part of polyester in the presence of 100 ppm of magnesium in the form of crystalline magnesium acetate (890 g of $(CH_3COO)_2Mg.4H_2O$) as the glycolysis catalyst, at atmospheric pressure and at the boiling point of the glycol. 2 parts of a glycolysate containing 65.8% of DGT are obtained and are concentrated to give 1.91 parts of a glycol solution containing 70% of DGT.

4.035 parts of anhydrous rectified methanol and 0.0048 part of magnesium methylate, that is to say 1,000 ppm of magnesium relative to the DGT, are added to this solution.

The temperature of the reaction mixture is raised to 70° C. under atmospheric pressure and this temperature is maintained for 2 hours. The temperature is then lowered to 25° C. over the course of 1 hour, after which the reaction mixture is kept at the latter temperature for 4 hours under atmospheric pressure.

After filtration and washing with methanol, the DMT produced is dissolved in 3.08 parts of methanol at 110° C. under a pressure of 3 bars. The solution obtained is then crystallized by lowering the temperature first from 110° C. to 65° C. in 50 minutes, and then from 65° to 20° C. in 70 minutes.

The DMT-methanol suspension obtained is then treated on a centrifuge filter.

The DMT filtered off is dried, melted and then rectified.

Per kg of scrap employed, 940 g of DMT having the following characteristics are obtained:
Colorless in the molten state;
SP (solidification point): 140.7° C.; and
Acidity (expressed as acetic acid): 0.003%.

EXAMPLE 2

A glycolysate containing 410 parts of DGT in the form of a molten glycolysate containing 62% of DGT at 100° C. is used as the starting material.

1,200 parts of anhydrous methanol and 2,000 ppm of magnesium in the form of freshly prepared magnesium methylate are added. The reaction mixture is then cooled to 30° C. and kept at this temperature for 9 hours.

394 parts of DMT, corresponding to 96% of the DGT employed, are obtained.

EXAMPLE 3

Example 1 is repeated, but with 250 ppm of magnesium in the form of the freshly prepared methylate. The DMT appears after 71 minutes and the yield of DMT at the end of the reaction is 81.5%, expressed relative to the scrap employed. This yield is calculated from the DMT formed during the methanol interchange reaction, without taking into account unconverted terephthalate residues which can be recycled in a subsequent operation and which are present in the methanol filtrates.

EXAMPLES 4 to 7

Example 1 is repeated, but with methanol containing 0.1% of water and with various contents of magnesium methylate, expressed as magnesium. The following results are obtained:

TABLE 1

| Examples | Catalyst in ppm of Mg | Appearance of DMT in Minutes | Yield of DMT, %* |
|---|---|---|---|
| 4 | 2,000 | 72 | 81.6 |
| 5 | 1,500 | 60 | 81.4 |
| 6 | 1,000 | 71 | 83.7 |
| 7 | 500 | 110 | 68.4 |

*Yield calculated as in Example 3.

EXAMPLE 8

Example 1 is repeated as far as the preparation of the glycolysate and the proportions of the reactants at all stages of the process are concerned, but the interchange is carried out continuously in an apparatus consisting of 4 reactors arranged in series. The glycolysate/methanol/catalyst reaction mixture is produced in the first reactor and is then passed continuously from one reactor to the next by overflowing, until a suspension of DMT in methanol is obtained.

The conditions of operation of each reactor are as follows:

|  |  | Temperature | Residence Time |
|---|---|---|---|
| Reactor 1: | Mixture | 70°–72° C. | 120 minutes |
| Reactor 2: | Cooling | 25° C. | 60 minutes |
| Reactor 3: | Delay | 25° C. | 120 minutes |
| Reactor 4: | Delay | 25° C. | 120 minutes |

The suspension obtained is treated as in Example 1.

The crystals of DMT obtained continuously are more homogeneous than those obtained discontinuously, which therefore simplifies the subsequent treatments.

Per kg of scrap employed, 945 g of DMT exhibiting the following characteristics are obtained:
Colorless in the molten state;
SP: 140.7° C.; and
Acidity (as acetic acid): 0.0025%

EXAMPLE 9

The glycolysis of copolyester scrap containing 50 mol % of ethylene terephthalate units and 50 mol % of ethylene isophthalate units is carried out.

For this purpose, 310 g of copolyester are treated with 360 g of ethylene glycol in the presence of 0.5 g of crystalline magnesium acetate as the glycolysis catalyst.

The mixture is heated to 205° C. in the course of one hour at atmospheric pressure.

A 60% strength glycolysate is obtained, which is concentrated to 70% of diglycol phthalates by distilling 100 g of ethylene glycol.

This glycolysate is treated with 920 g of methanol containing 300 ppm of water and 0.6 g of magnesium in the form of the methylate (representing 1,500 ppm of magnesium relative to the diglycol phthalates).

The temperature of the reaction mixture is raised to 70° C. under atmospheric pressure, and this temperature is maintained for one hour. The temperature is lowered to 25° C. in the course of oe hour and the mixture is then maintained at this temperature for two hours at atmospheric pressure. The DMT crystallizes slowly. It is recovered by filtration, a second portion of DMT is recovered in the methanol mother liquor after standing for several hours.

The DMT obtained has a solidification point of 139° C.

The dimethyl isophthalate remains in solution in the methanol.

EXAMPLE 10

A poly(hexamethylene terephthalate) is subjected to hexanediolysis. For this purpose, 248 g of the polyester are treated with 362 g of hexane-1,6-diol in the presence of 0.5 g of crystalline magnesium acetate under atmospheric pressure for 1 hour 30 minutes. The diolysate obtained contains 60% of bis-hexanediol terephthalate (BHT). It is concentrated to 70% strength by distilling 87 g of hexanediol.

The diolysate obtained is treated with 840 g of methanol containing 20 ppm of water and 55 g of a catalyst solution containing 1% of magnesium methylate in methanol (representing 1,500 ppm of magnesium relative to the BHT). The temperature of the reaction mixture is raised to 70° C. and is maintained thereat for one hour. The temperature is then lowered to 25° C. in the course of one hour after which the mixture is left to stand overnight.

The DMT obtained, which contains 86.7% of pure DMT, is filtered off, washed with methanol, and crystallized again.

EXAMPLE 11

The hexanediolysis of Example 10 is repeated, but under a pressure of 150 mm Hg. After concentrating the diolysate obtained to a 70% content of BHT, it is treated with 840 g of methanol containing 20 ppm of water and 110 g of the same catalyst solution as in Example 10, representing 3,000 ppm of magnesium relative to the BHT.

The temperature of the reaction mixture is raised to 70° C., maintained thereat for one hour, and then lowered from 70° to 25° C. in the course of one hour, after which the mixture is left at the latter temperature for two hours under atmospheric pressure.

The DMT obtained, which contains 90.7% of pure DMT, is filtered off, washed, crystallized again and dried.

EXAMPLE 12

The butanediolysis of a poly(butylene terephthalate) is carried out. For this purpose, 220 g of poly(butylene terephthalate) are treated with 296 g of butanediol in the presence of 0.5 g of crystalline magnesium acetate under a pressure of 150 mm Hg for 2 hours and 15 minutes at a temperature between 180° and 190° C. 516 g of a diolysate containing 60% of bis-(butanediol) terephthalate (BBT) are obtained, and are concentrated to 70% strength by distilling 74 g of butanediol.

The 70% strength diolysate is treated with 900 g of methanol containing 200 ppm of water in the presence of 200 g of a catalyst solution containing 1% of magnesium methylate in methanol, representing 7,000 ppm of magnesium relative to the BBT.

The temperature of the reaction mixture is raised to 70° C. and this temperature is maintained for one hour. The temperature is then lowered from 70° to 25° C. in the course of one hour, after which the mixture is maintained at this temperature at atmospheric pressure overnight.

After filtration, washing with methanol and drying, 103 g of DMT containing 84% of pure product and having a solidification point of 137.6° C. before further purification, are obtained.

What is claimed is:

1. A process for converting a bis-(diol) terephthalate obtained by diolysis of a polyterephthalate or copolyterephthalate, to dimethyl terephthalate by interchange in a substantially anhydrous methanol medium in the presence of magnesium methylate as the catalyst.

2. A process according to claim 1, in which the amount of methanol is at least equal to, and preferably between two and three times, the weight of the bis-(diol) terephthalate to be converted.

3. A process according to claim 1, in which the reaction is carried out in the presence of at least 250 ppm of magnesium, in the form of magnesium methylate, relative to the weight of the bis-(diol) terephthalate to be converted.

4. A process according to claim 3, in which the reaction is carried out in the presence of at least 1,000 ppm of magnesium, in the form of magnesium methylate, relative to the weight of the bis-(diol) terephthalate to be converted.

5. A process according to claim 1, in which the reaction is carried out at a temperature between ordinary temperature and the boiling point of the mixture.

6. A process according to claim 5, in which the reaction is carried out under pressure.

7. A process according to claim 5, in which the reaction is effected in two stages, the first one wherein the bis (diol) terephthalate is converted into a mixed methyl/diol terephthalate being carried out at a temperature between room temperature and the boiling point of the mixture, and the second one wherein said mixed methyl/diol terephthalate is converted into dimethylterephthalate being carried out at ordinary temperature or in the course of cooling to that temperature.

8. A process according to claim 7, in which the first stage is carried out at atmospheric pressure and at a temperature of about 70° C., and the second stage terminates at about 25° C.

9. A process according to claim 8, in which the reaction is carried out in several reactors arranged in series, the first reactor being maintained at the boiling point of the reaction mixture and the remaining reactors at ordinary temperature and the reaction mixture, produced continuously in the first reactor, passes in cascade from one reactor to the next.

10. A process according to claim 1, in which the bis-(diol) terephthalate is bis-(ethylene glycol) terephthalate.

11. A process according to claim 1, in which the bis-(diol) terephthalate is bis-(propanediol) terephthalate.

12. A process according to claim 1, in which the bis-(diol) terephthalate is bis-(butanediol) terephthalate.

13. A process according to claim 1, in which the bis-(diol) terephthalate is bis-(hexanediol) terephthalate.

14. A process according to claim 1, in which the bis-(diol) terephthalate is bis-(cyclohexyldimethanol) terephthalate.

* * * * *